United States Patent
Muehlig et al.

(10) Patent No.: US 7,256,887 B2
(45) Date of Patent: Aug. 14, 2007

(54) DETERMINING THE SUITABILITY OF AN OPTICAL MATERIAL FOR THE PRODUCTION OF OPTICAL ELEMENTS, CORRESPONDING DEVICE, AND USE OF SAID MATERIAL

(75) Inventors: Christian Muehlig, Jena (DE); Wolfgang Triebel, Jena-Cospeda (DE); Jochen Alkemper, Kleinwinternheim (DE); Regina Martin, Jena (DE)

(73) Assignee: Schott AG, Mainz (DE)

( * ) Notice: Subject to any disclaimer, the term of this patent is extended or adjusted under 35 U.S.C. 154(b) by 107 days.

(21) Appl. No.: 10/527,850

(22) PCT Filed: Sep. 16, 2003

(86) PCT No.: PCT/DE03/03069

§ 371 (c)(1),
(2), (4) Date: Jun. 23, 2005

(87) PCT Pub. No.: WO2004/027395

PCT Pub. Date: Apr. 1, 2004

(65) Prior Publication Data

US 2005/0237523 A1   Oct. 27, 2005

(30) Foreign Application Priority Data

Sep. 16, 2002   (DE) .............................. 102 42 934
Aug. 2, 2003    (DE) .............................. 103 35 456

(51) Int. Cl.
*G01N 21/64* (2006.01)
(52) U.S. Cl. ..................... 356/318; 250/458.1
(58) Field of Classification Search ................ 356/318; 250/458.1, 459.1, 461.1
See application file for complete search history.

(56) References Cited

U.S. PATENT DOCUMENTS 3,824,402 A * 7/1974 Mullaney et al. ........ 250/458.1
2001/0043331 A1   11/2001 Rebhan

FOREIGN PATENT DOCUMENTS

| DE | 27 47 409 | 4/1978 |
| DE | 28 00 415 | 7/1978 |
| WO | WO 98/08775 | * 3/1998 |
| WO | 02/48694 A1 | 6/2002 |

OTHER PUBLICATIONS

W. Triebel et al: "Evaluation of Fused Silica . . . " Proceesings of SPIE vol. 4103, 2000, pp. 1-11.
M. Mizuguchi et al: Generation of Optical Absorption Bands . . . J Vac. Sci. Tehnol. A 16(5) Sep./Oct. 1998, pp. 3052-3057.
M. Mizuguchi et al: "Time-Resolved Photoluminescence for . . . " J. Opt. Soc. Am. B. vol. 16, No. 7, Jul. 1999, pp. 1153-1159.
K. Mann et al: "Optical Metrology in the VUV and . . . " Proceedings of SPIE vol. 4779, 2002, pp. 31-40.

* cited by examiner

Primary Examiner—F. L. Evans
(74) Attorney, Agent, or Firm—Michael J. Striker

(57) ABSTRACT

The method tests the suitability of an optical material having a radiation-induced absorption, especially of an alkali or alkaline earth halide, for production of an optical element exposed to high-energy irradiation. The method includes pre-irradiating the optical material with laser radiation until rapid damage induced in the optical material with the laser radiation is saturated; subsequently measuring fluorescence of the optical material during and/or immediately after irradiating the optical material with excitation radiation and determining the non-intrinsic fluorescence and intrinsic fluorescence present in the measured fluorescence. Suitability may be preferably determined according to a ratio of the amount of non-intrinsic fluorescence to intrinsic fluorescence. A device for performing the method including a barrier device for blocking scattered excitation radiation is also provided.

17 Claims, 1 Drawing Sheet

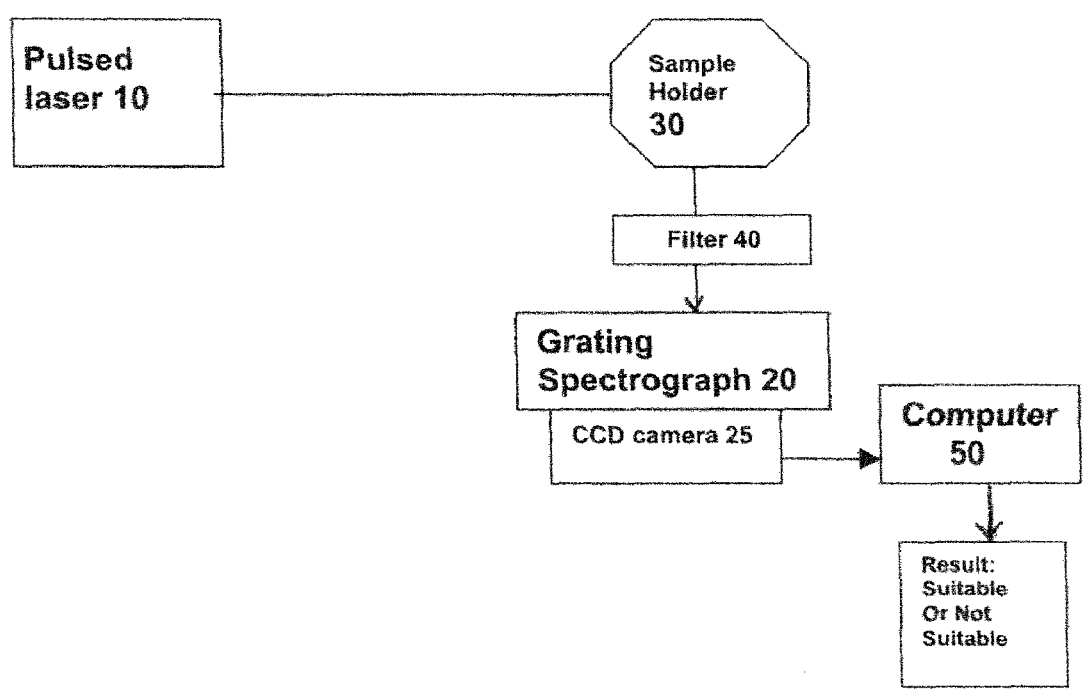

DETERMINING THE SUITABILITY OF AN OPTICAL MATERIAL FOR THE PRODUCTION OF OPTICAL ELEMENTS, CORRESPONDING DEVICE, AND USE OF SAID MATERIAL

CROSS-REFERENCE

This is the U.S. National Stage of PCT/DE 03/03069, which has an International filing date of Sep. 16, 2003, and on which a claim of priority under 35 U.S.C. 363 is based.

BACKGROUND OF THE INVENTION

1. The Field of the Invention

The present invention relates to a method for determining the suitability of an optical material for the production of optical elements, to a device for carrying out the method, and to the optical elements made from the optical materials determined to be suitable using the method.

2. Related Art

It is known that materials used to produce optical elements absorb irradiating light to a greater or lesser extent, so that the intensity of the light and/or radiation is typically less after it passes through an optical element than before it passes through. It is also known that the extent of this absorption depends on the wavelength of the light. For optical systems, i.e., for optically transparent systems, the goal, however, is to keep the absorption as low as possible, i.e., they should have a high light permeability or transmission, at least for the particular working wavelength. The absorption is composed of material-specific (intrinsic) portions and portions due to "non-intrinsic" portions, such as inclusions, contamination and/or crystal imperfections. While the intrinsic absorption is independent of the particular quality of the material, the additional radiation absorption of the non-intrinsic absorption results in a degradation of the optical material.

As a result of the intrinsic and non-intrinsic absorption, energy is deposited in the optical material, which results in a temperature rise. The disadvantage of the material heating in this manner is that the optical properties, e.g., the refractive index, change, which results in a change in the reproduction ratios in an optical component used for beam shaping, for example, since the refractive index depends not only on the wavelength of the light, but also on the temperature of the optical material. In addition, a temperature rise in an optical component also results in a change in the lens geometry. These phenomena produce a change in the lens focal point and blurriness in images projected with the heated lens. In photolithography in particular, which is used to produce computer chips and electronic circuits, this results in quality degradations and/or an increase in waste, and is therefore not desired.

With many materials, a portion of the absorbed radiation is not only converted to heat, but is also given off again in the form of fluorescence. The formation of fluorescence on optical materials, in particular on optical crystals, is known per se. For example, W. Triebel et al. describe, in Proceedings SPIE Vol. 4103, pages 1-11, 2000 Triebel, Bark-Zollmann, Mühlig et al. in "Evaluation of Fused Silica for DUV Laser Applications by Short Time Diagnostics", the formation and measurement of laser-induced fluorescence (LIF) in quartz, particularly in OH-rich quartz and/or a glass matrix. Furthermore, M. Mizuguchi et al. describe, in J. Vac. Sci. Technol. A., Vol. 16, pages 2052-3057 (1998), the formation of optical absorption bands in a calcium fluoride crystal. In addition, M. Mizuguchi et al. describe, in J. Opt. Soc. Am. B, Vol. 16, pages 1153-1159, July 1999, a time-resolved photoluminescence for diagnosing the laser damage done to a calcium fluoride crystal. This article describes the formation of color centers that form photoluminescence via excitation with an ArF excimer laser at 193 nm. To enable measurements of this type, however, crystals with a relatively high amount of impurities are used in this case, and this does not fulfill the high requirements for photolithography. In addition, the fluorescence measurement is carried out in the sample to be investigated after a waiting period of 50 nsec after the laser pulse ends. It has been shown that the fluorescence values obtained in this manner cannot be used for quality control purposes or to determine the extent of the impurity, and therefore cannot be used to form color centers in the high-quality crystals.

It is therefore believed that the determination of radiation-induced fluorescence, in particular laser-induced fluorescence, cannot be used for quality control of high-quality, optical materials, as with high-purity calcium fluoride for photolithography, for example. (Refer also to the presentation by Dr. Mann, Laserlabor Göttingen, SPIE Conference in Seattle, USA, July 2002). It was determined that a correlation cannot be made between laser-induced fluorescence and a claim regarding impurities and the optical quality of a material.

SUMMARY OF THE INVENTION

The object of the present invention, therefore, is to provide a test with which an optical material can be tested for its suitability for use as an optical element and, in fact, tested in general for use at certain working wavelengths. The test should be easy to perform and require very little equipment. Finally, it should be possible to carry out the test with as little background as possible, i.e., the results should contain no background effects, if possible, and it should be possible to carry out the test with very high sensitivity. In addition, it should be possible to also determine, in the most selective manner possible, interference by impurities in high quality crystals that are present in small amounts and are impossible or very difficult to detect, and to assign them to the particular contaminating substance.

In addition, it should be possible, using the method, to determine the amount and type of impurity in the particular sample, regardless of the sample size, and without extensive calibration.

All of these objectives are attained by the method and device defined in the claims.

According to the present invention, it was found that the problems of the related art cited above can be prevented by determining the non-intrinsic fluorescence during excitation with light and/or immediately after a light pulse ends, i.e., after the light pulse has passed through the sample. It has been shown that, with measurements carried out according to the related art, the non-intrinsic fluorescences have already decayed greatly due to their short lives, which are in the nanosecond range. For this reason, these measurements contain only very slight non-intrinsic fluorescence signals.

This is avoided with the method according to the present invention and by optimizing the non-intrinsic fluorescence signals. The radiation-induced absorption and, in particular, the absorption induced by flaws and/or impurities can be easily characterized in this manner.

In a preferred embodiment according to the present invention, the intrinsic fluorescence is determined in addition to the non-intrinsic fluorescence, for standardization purposes. Since, in fact, the intrinsic fluorescence is a material constant, the size ratio of non-intrinsic to intrinsic fluorescence can be used to standardize the non-intrinsic bands and thereby quickly determine whether the optical material being tested is suitable for further processing to an optical element such as a lens, prism, etc. In addition, this ratio can be used—with reference to a simple calibration curve—to determine the amount of a particular impurity at any time without the need to perform elaborate calibrations, e.g., dimension determinations, etc., on the sample to be investigated.

Non-intrinsic fluorescence bands are preferably used to carry out the method according to the present invention. Preferred non-intrinsic bands are those at wavelengths 313 nm, 333 nm, 365 nm, 420 nm, 450 nm, 500 nm, 580 nm, 740 nm and 225 nm. It was found that the fluorescence wavelength 225 nm is produced only at irradiation with a wavelength of 157 nm ($F_2$ laser), although this does not exist in every material. Highly preferred, however, is the determination of fluorescence at the wavelength 580 and/or 740 nm. These fluorescence bands are typically found and have proven to be particularly sensitive in the method according to the present invention. The fluorescence at 450 nm is also particularly crucial. This band is not as sensitive to the fluorescence and/or irradiated energy density, although it has a noticeably strong influence on the initial transmission $T_o$. According to the present invention, when an intrinsic fluorescence band occurs, it is used to standardize the non-intrinsic fluorescence. The intrinsic fluorescence band at 278 nm is preferably used for standardization. It has been shown that this band is free of other non-intrinsic components. For this reason, it is particularly well-suited for standardization. The standardization of the level of the measured, non-intrinsic fluorescence band or bands is carried out by calculating the ratio of non-intrinsic to intrinsic fluorescence. Of particular preference in the method according to the present invention, the non-intrinsic fluorescence is determined synchronously with the irradiated laser pulse.

It has proven particularly advantageous to treat the material to be determined with pre-irradiation before carrying out the method according to the invention. In this procedure, a predetermined number of laser pulses is used to determine the absorption state of the material with regard for "rapid damage" and/or "rapid annealing", so that each of the subsequent measurements is carried out from one even base level. Typical pulse amounts for ArF lasers (193 nm) are at least 3000, preferably at least 6000, and, with an irradiation wavelength of 157 nm ($F_2$ laser), they are 30,000, and preferably 70,000-200,000 laser pulses. In principle, to carry out the method according to the present invention, it is necessary to irradiate the material to be investigated with the most comparable energy densities possible. The method is also preferably carried out not only with the same or a comparable energy density, but also preferably at the same excitation and fluorescence wavelengths to obtain comparable values and spectra, in particular.

With the method according to the present invention it is also possible to test the suitability of an optical material for any excitation wavelength and, in fact, before any type of further processing to form an optical element or component. It is possible, for example, to determine the exact intrinsic fluorescence at an excitation wavelength of 193 nm and 157 nm and to take it into account in the determination of the non-intrinsic fluorescence and to thereby classify the optical material as suitable for one or the other wavelength, depending on the application.

Finally, the type of impurities can also be easily determined, even in amounts in the ppb range, from the fluorescence spectrum. Based on the ratio of intrinsic to non-intrinsic fluorescence, it is also possible to determine the amount of impurity that is producing the fluorescence. Typical contaminating-materials are rare earths and, in particular, Cer, europium, terbium, sodium and oxidic oxygen.

According to the present invention, the determination method is preferably carried out with UV light and, in particular, deep UV light. Wavelengths below 250 nm, in particular below 200 nm, have proven advantageous, and wavelengths between 100 and 150 nm and 200 nm are particularly preferred. Advantageously, the method is carried out at the excitation wavelength with which the optical material will be irradiated during subsequent use. A preferred radiation source for the high-energy light is a laser, whereby laser pulses with working wavelengths of 193 and/or 157 nm are preferred.

In the method according to the present invention, the non-intrinsic fluorescence is preferably measured with a grating spectrograph and an I-CCD camera (intensified charged coupled device) with adjustable illumination intervals, whereby it is preferable to use a computer to process the spectrum obtained. Measurements and devices of this type are known to one skilled in the art, and are described, for example, by W. Triebel et al. in Proceedings SPIE Vol. 4103, pages 1 through 11, 2000, "Evaluation of Fused Silica for DUV Laser Applications by Short Time Diagnostics", and by Mizuguchi et al. in J. Opt. Soc. Am. B, Vol. 16, 1153 ff. (July 1999).

It is particularly preferred according to the present invention to locate a barrier device between the fluorescent sample to be investigated and the fluorescence measurement device, the barrier device preventing passage by the typically high-energy excitation radiation. Barrier devices of this type that hide any excitation wavelengths are known to one skilled in the art. The hiding can take place in any manner. One possibility is for these wavelengths to be hidden using a grating spectrograph located in front of the CCD camera that divides the absorbed light into its various wavelengths. By locating and/or rotating the spectrograph accordingly, it is possible to block or deflect the excitation wavelength separated out of a high-energy radiation source. It is also possible, in principle, to rotate the grating spectrographs of the CCD camera itself.

A further possibility is to use wavelength-specific filters, such as dielectric thin-layer filters, which can also be produced in a selective manner today for any wavelength. Filters of this type are typically produced by applying a corresponding multilayer reflective layer on a carrier material that prevents passage by the undesired wavelengths.

Layer filters of this type are preferred in the method according to the present invention. It is also necessary, however, that the filters used not have any intrinsic fluorescence produced by the incident light, so that the measured results are not adulterated.

With the method according to the present invention, it is now possible to determine fluorescences, the wavelengths of which are close to the excitation wavelength. This is particularly significant for the use of optical elements in photolithography, since the energy of fluorescence at wavelengths of this type is also sufficient to expose the photosensitive resist of a wafer, which results in a strong loss of contrast in the circuit pattern projected onto the wafer.

The determination of the fluorescence according to the present invention preferably takes place within or immediately after an exposure interval on the material. It takes place preferably within a time segment after the material exposure has ended, the time segment corresponding to the particular characteristic decay curves and/or lives of the various non-intrinsic fluorescences, and/or is adapted thereto. In a large number of cases, 90%, in particular 80% and often 70% of the decay time has proven advantageous for the measurement. In a few preferred optical materials, the method according to the present invention and/or the determination is carried out within a time period and/or time segment of less than 50 nsec after the irradiation and/or the irradiation pulse in the material ends, whereby the determinations of up to max. 40 and preferably up to max. 30 nsec are particularly preferred. In a few cases, measurements within a time of less than 15 nsec have even proved advantageous, after the radiation pulse has passed through the material.

Of the CCD cameras used in the method according to the present invention, "OMAs" (optical multichannel analyzers) are preferred, particularly when they have adjustable exposure and/or measurement intervals. A camera of this type has a detection limit of less than 10 photons and therefore enables short exposure times, e.g., of 10 nsec or even as short as 150 psec. Cameras of this type are commercially available from Roper Scientific, USA, for example.

The method according to the present invention is suitable for use with any optical materials that develop a fluorescence when irradiated, whereby crystalline, optical materials are preferred, in particular halogenidic and/or fluoridic monocrystals. Particularly preferred are alkaline and/or earth alkaline fluorides, whereby calcium fluoride, barium fluoride, strontium fluoride, lithium fluoride, potassium fluoride, sodium fluoride and/or magnesium fluoride and a mixture, such as $KMgF_3$ are very preferably preferred.

BRIEF DESCRIPTION OF THE DRAWING

The following sole FIGURE is a diagrammatic representation of a preferred device for carrying out the method of determining the suitability of a crystalline optical material, especially an alkali or alkaline earth halide crystal, for making an optical element, especially an optical element for photolithograph.

The present invention also relates to a device for carrying out a particularly preferred method according to the present invention. A device of this type includes a radiation source, especially a pulsed laser 10, for transmitting excitation radiation at an excitation wavelength, a sample holder 30 for holding a material sample to be determined, and a device for measuring a flourescence intensities of fluorescence induced in the material sample by the excitation radiation. The excitation radiation travels along a typically linear beam path that starts at the radiation source, through the material sample, and preferably enters a reference photodiode. According to the present invention, the fluorescence determination device is located outside this beam path, so that no radiation of the excitation wavelength can strike the fluorescence determination device directly. The device is preferably arranged such that the fluorescence to be measured describes a fluorescence beam path that extends perpendicularly to the excitation beam path. The fluorescence measurement device typically includes one or more optical lenses that bundle the fluorescence emitted by the material sample to be investigated in a polychromator and/or a grating spectrograph 20. The fluorescent light that is broken down into its individual wavelengths in the spectrograph is then deflected to a CCD camera 25, In particularly an I-CCD, in which the intensities at the individual wavelengths are determined and are preferably processed and stored using a computer 50 and/or a data processing system. The fluorescence intensities determined and stored in this manner using the CCD camera can be easily compared with stored standard values and analyzed by the computer.

The device according to the present invention is unique in that a barrier element is located between the material sample to be tested and the CCD camera that prevents the high-energy excitation radiation from passing through to the CCD camera. The barrier element located in the device according to the present invention insures that no light from the radiation source reaches the CCD camera. The barrier element also prevents scattered light from the excitation wavelength from reaching the CCD camera, which could not only falsify the measurement but also destroy this highly sensitive camera. The barrier element used according to the present invention should not fluoresce itself at the excitation wavelengths and thereby falsify measured fluorescent values.

All types of devices that deflect, reflect or absorb a certain wavelength are suitable for use as the barrier element. The simplest configuration is an optical grating, for example, as included in a polychromator and/or spectrographs. In a further preferred exemplary embodiment according to the present invention, the barrier element includes a wavelength-specific filter 40, in particular a multilayer filter, In the case of which a double layer or multiple reflective layers are applied that blank out or reflect the particular wavelength. A particularly preferred filter is a dielectric thin-layer filter.

It has been shown that it is possible with filters of this type to also determine fluorescences that are close to the excitation wavelength. Fluorescences of this type are fatal with photolithography in particular, since they can expose a photosensitive resist due to their vicinity to the excitation wavelength, just like the excitation wavelength itself, and therefore noticeably reduce the sharpness and/or contrast of a projected circuit pattern.

With the method according to the present invention it is therefore possible in the production of optical devices to not only exclude, at an early stage, optical materials from further processing that have high non-intrinsic fluorescence but also those that have a fluorescence close to the excitation wavelength.

The optical materials determined according to the present invention are particularly suited to the production of optical components in DUV lithography, and to the production of wafers coated with photosensitive resist and, therefore to the production of electronic devices. The present invention therefore also relates to the use of materials obtained using the method according to the present invention and/or in the device according to the present invention in the production of lenses, prisms, light-conducting rods, optical windows and optical devices for DUV lithography, in particular in the production of steppers and excimer lasers and, therefore, to the production of integrated circuits, computer chips and electronic devices such as computers and other devices that contain chip-like integrated circuits.

What is claimed is:

1. A method of determining suitability of a crystalline optical material for production of an optical element, particularly for high-energy irradiation, wherein radiation-induced absorption is detected or identified in the optical material, said method comprising the steps of:
    a) pre-irradiating the crystalline optical material with laser radiation until rapid damage induced in the crystalline optical material with the laser radiation is saturated;
    b) after the pre-irradiating of step a), measuring total fluorescence produced in the crystalline optical material by excitation radiation during and/or immediately after irradiating the crystalline optical material with the excitation radiation, said total fluorescence being composed of intrinsic fluorescence and non-intrinsic fluorescence;
    c) determining the non-intrinsic fluorescence of the crystalline optical material in the total fluorescence measured during and/or immediately after irradiating with the excitation radiation;
    d) determining the intrinsic fluorescence of the crystalline optical material, said intrinsic fluorescence being a constant of said crystalline optical material;
    e) determining an amount ratio of said non-intrinsic fluorescence to said intrinsic fluorescence in said total fluorescence measured in step b);

f) ascertaining whether or not said optical material is suitable for making said optical element according to said amount ratio determined in step e); and g) outputting whether or not said optical material is suitable for making said optical element according to said amount ratio.

2. The method as defined in claim 1, wherein the crystalline optical material is irradiated by the excitation radiation for a short period of time.

3. The method as defined in claim 1, wherein the excitation radiation comprises at least one laser pulse.

4. The method as defined in claim 1, wherein the total fluorescence is measured with an I-CCD camera.

5. The method as defined in claim 1, wherein the total fluorescence is measured using a grating spectrograph.

6. The method as defined in claim 1, wherein the excitation radiation has an excitation radiation wavelength and during the measuring of the total fluorescence of the optical material by a measuring device radiation emitted from the optical material at the excitation radiation wavelength is prevented from reaching the measuring device by a barrier device.

7. The method as defined in claim 6, wherein the barrier device is a radiation filter and/or a spectral grating.

8. The method as defined in claim 1, wherein the total fluorescence is measured after halting the irradiating of the optical material with the excitation radiation during a time interval in which the non-intrinsic fluorescence decays.

9. The method as defined in claim 1, wherein the crystalline optical material is $CaF_2$, $BaF_2$, $SrF_2$, LiF, NaF, $MgF_2$ or $KMgF_3$.

10. The method as defined in claim 1, wherein the intrinsic fluorescence comprises intrinsic fluorescence bands, the non-intrinsic fluorescence comprises non-intrinsic fluorescence bands and one of said intrinsic fluorescence bands is used to standardize the non-intrinsic fluorescence bands.

11. The method as defined in claim 1, wherein radiation energy densities of the excitation radiation are comparable to those of the radiation-induced absorption.

12. The method as defined in claim 1, further comprising measuring the total fluorescence with a measuring device and wherein said measuring device comprises a source for propagating the excitation radiation along a predetermined light path; a holder for a material sample to be measured arranged in the predetermined light path; means for measuring fluorescence intensities of light emitted from the material sample when the material sample is held in the holder, said means for measuring fluorescence intensities being arranged off the predetermined light path, and a barrier device located between the holder and the means for measuring fluorescence intensities, said barrier device comprising means for preventing radiation from the material sample having a wavelength that is the same as that of the excitation radiation from reaching the means for measuring fluorescence intensities.

13. The method as defined in claim 12, wherein said source for propagating said excitation radiation is a pulsed laser, the means for measuring fluorescence intensities is a grating spectrograph equipped with a CCD camera, and the barrier device is a dielectric thin-layer filter.

14. A method of determining suitability of an alkaline or alkaline earth fluoride monocrystal for making an optical element for high-energy irradiation, wherein radiation-induced absorption is detected or identified in the monocrystal, said method comprising the steps of:

a) pre-irradiating the alkaline or alkaline earth fluoride monocrystal with laser radiation until rapid damage induced in the alkaline or alkaline earth fluoride monocrystal with the laser radiation is saturated;

b) after the pre-irradiating of step a), measuring total fluorescence produced in the alkaline or alkaline earth fluoride monocrystal by excitation radiation at an excitation radiation wavelength below 200 nm by means of a fluorescence measuring device during and/or immediately after irradiating the alkaline or alkaline earth fluoride monocrystal with the excitation radiation, said total fluorescence being composed of intrinsic fluorescence and non-intrinsic fluorescence;

c) during the measuring of the total fluorescence, preventing ultraviolet radiation at the excitation radiation wavelength propadated toward the fluorescence measuring device from reaching the measuring device by means of a barrier device;

d) determining the non-intrinsic fluorescence of the alkaline or alkaline earth fluoride monocrystal in the total fluorescence measured during and/or immediately after irradiating with the excitation radiation;

e) determining the intrinsic fluorescence of the alkaline or alkaline earth fluoride monocrystal, said intrinsic fluorescence being a constant of said alkaline or alkaline earth fluoride monocrystal;

f) determining an amount ratio of said non-intrinsic fluorescence to said intrinsic fluorescence in said total fluorescence measured in step b);

g) ascertaining whether or not said alkaline or alkaline earth fluoride monocrystal is suitable for making said optical element according to said amount ratio determined in step e); and h) outputting whether or not said optical material is suitable for making said optical element according to said amount ratio.

15. The method as defined in claim 14, wherein said barrier device is a wavelength-specific dielectric thin-layer filter.

16. The method as defined in claim 1, wherein said optical element is a lens, a prism, a light-conducting rod or an optical window for DUV photolithography, for steppers, for excimer lasers, for wafers, for computer chips, for integrated circuits, and for electronic devices that contain said integrated circuits and said computer chips.

17. The method as defined in claim 14, wherein said optical element is a lens, a prism, a light-conducting rod or an optical window for DUV photolithography, for steppers, for excimer lasers, for wafers, for computer chips, for integrated circuts, and for electronic device that contain said integrated circuits and said computer chips.

* * * * *